(12) United States Patent
Piestun et al.

(10) Patent No.: US 8,693,742 B2
(45) Date of Patent: Apr. 8, 2014

(54) THREE-DIMENSIONAL SINGLE-MOLECULE FLUORESCENCE IMAGING BEYOND THE DIFFRACTION LIMIT USING A DOUBLE-HELIX POINT SPREAD FUNCTION

(75) Inventors: Rafael Piestun, Golden, CO (US); Sri Rama Prasanna Pavani, Pasadena, CA (US); Michael A. Thompson, Orange, CA (US); Julie S. Biteen, Menlo Park, CA (US); William E. Moerner, Los Altos, CA (US)

(73) Assignee: The Regents of the University of Colorado, Denver, CO (US)

( * ) Notice: Subject to any disclaimer, the term of this patent is extended or adjusted under 35 U.S.C. 154(b) by 977 days.

(21) Appl. No.: 12/640,834

(22) Filed: Dec. 17, 2009

(65) Prior Publication Data
US 2010/0278400 A1 Nov. 4, 2010

Related U.S. Application Data

(60) Provisional application No. 61/138,462, filed on Dec. 17, 2008.

(51) Int. Cl.
*G06K 9/00* (2006.01)
*G06K 9/62* (2006.01)

(52) U.S. Cl.
USPC .......................................... 382/128; 382/100

(58) Field of Classification Search
USPC ....................................................... 382/128
See application file for complete search history.

(56) References Cited

U.S. PATENT DOCUMENTS

| | | |
|---|---|---|
| 3,054,898 A | 9/1962 | Westover et at |
| 3,597,083 A | 8/1971 | Fraser |
| 3,901,595 A | 8/1975 | Helava et al. |
| 3,061,851 A | 6/1976 | Gerharz |
| 4,178,090 A | 12/1979 | Marks et al. |
| 4,573,191 A | 2/1986 | Kidode et al. |
| 4,794,550 A | 12/1988 | Greivenkamp, Jr. |
| 4,825,263 A | 4/1989 | Desjardins et al. |
| 4,843,631 A | 6/1989 | Steinpichler et al. |
| 5,076,687 A | 12/1991 | Adelson |
| 5,102,223 A | 4/1992 | Uesugi et al. |
| 5,193,124 A | 3/1993 | Subbarao |
| 5,243,351 A | 9/1993 | Rafanelli et al. |
| 5,337,181 A | 8/1994 | Kelly |
| 5,521,695 A | 5/1996 | Cathey et al. |

(Continued)

OTHER PUBLICATIONS

Juette, Three-dimensional sub-1 O0 nm resolution fluorescence microscopy of thick samples, 2008, Nat Methods 5:527-529.*

(Continued)

*Primary Examiner* — Tran Nguyen
(74) *Attorney, Agent, or Firm* — Maschoff Brennan

(57) ABSTRACT

Embodiments of the present invention can resolve molecules beyond the optical diffraction limit in three dimensions. A double-helix point spread function can be used to in conjunction with a microscope to provide dual-lobed images of a molecule. Based on the rotation of the dual-lobed image, the axial position of the molecule can be estimated or determined. In some embodiments, the angular rotation of the dual-lobed imaged can be determined using a centroid fit calculation or by finding the midpoints of the centers of the two lobes. Regardless of the technique, the correspondence between the rotation and axial position can be utilized. A double-helix point spread function can also be used to determine the lateral positions of molecules and hence their three-dimensional location.

19 Claims, 12 Drawing Sheets

(56) References Cited

U.S. PATENT DOCUMENTS

| | | | |
|---|---|---|---|
| 6,344,893 | B1 | 2/2002 | Mendlovic et al. |
| 6,969,003 | B2 | 11/2005 | Havens et al. |
| 2003/0061035 | A1 | 3/2003 | Kadambe |
| 2005/0057744 | A1 | 3/2005 | Pohle et al. |
| 2006/0126921 | A1* | 6/2006 | Shorte et al. .......... 382/154 |
| 2007/0268366 | A1 | 11/2007 | Raskar et al. |

OTHER PUBLICATIONS

Aguet, Francois et al., "A Maximum-Likelihood Formalism for Sub-Resolution Axial Localization of Fluorescent Nanoparticles," Optics Express, vol. 13, No. 26, pp. 10503-10522, Dec. 26, 2005.

Chasles, F. et al., "Full-Field Optical Sectioning and Three-Dimensiona Localization of Fluorescent Particles Using Focal Plane Modulation," Optics Letters, vol. 31, No. 9, pp. 1274-1276, May 1, 2006.

Dowski, Jr., Edward R. et al., "Single-Lens Single-Image Incoherent Passive-Ranging Systems," Applied Optics, vol. 33, No. 29, pp. 6762-6773. Oct. 10, 1994.

Greengard, Adam et al, "Depth From Diffracted Rotation," Optics Letters, vol. 31, No. 2, pp. 181-183, Jan. 15, 2006.

Greengard, Adam et al., "Depth From Rotating Point Spread Functions," Proceedings of SPIE, vol. 5557, pp. 91-97, 2004.

Greengard, Adam et al., "Fisher Information of 3D Rotating Point Spread Functions," Computational Optical Sensing and Imaging Presentation, 31 pages, Jun. 6, 2005.

Johnson, Gregory E. et al., "Passive Ranging Through Wave-Front Coding: Information and Application," Applied Optics, vol. 39, No. 11, pp. 1700-1710. Apr. 10, 2000.

Kao, H. Pin et al., "Tracking of Single Fluorescent Particles in Three Dimensions: Use of Cylindrical Optics to Encode Particle Position," Biophysical Journal, vol. 67, pp, 1291-1300, Sep. 1994.

Pentland, Alex Paul, "A New Sense for Depth of Field," IEEE Transactions on Pattern Analysis and Machine Intelligence, vol. PAMI-9, No. 4, pp. 523-531, Jul. 1987.

Piestun, Rafael et al., "Wave Fields in Three Dimensions: Analysis and Synthesis," J. Opt. Soc. Am. A., vol. 13, No. 9, pp. 1837-1848. Sep. 1996.

Sirat, Gabriel Y, "Conoscopic Holography. I. Basic Principles and Physical Basis," J. Opt. Soc. Am. A, vol. 9, No. 1, pp. 70-83. Jan. 1992.

Subbarao, Murali et al., "Analysis of Defocused Image Data for 3D Shape Recovery Using a Regularization Technique," SPIE, vol. 3204, pp. 24-35, 1997.

\* cited by examiner

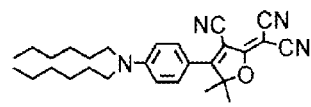
*FIG. 3A*
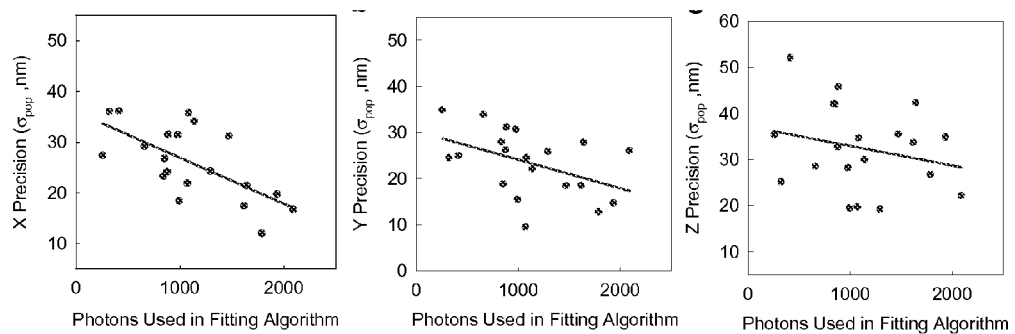
*FIG. 3B*  *FIG. 3C*  *FIG. 3D*

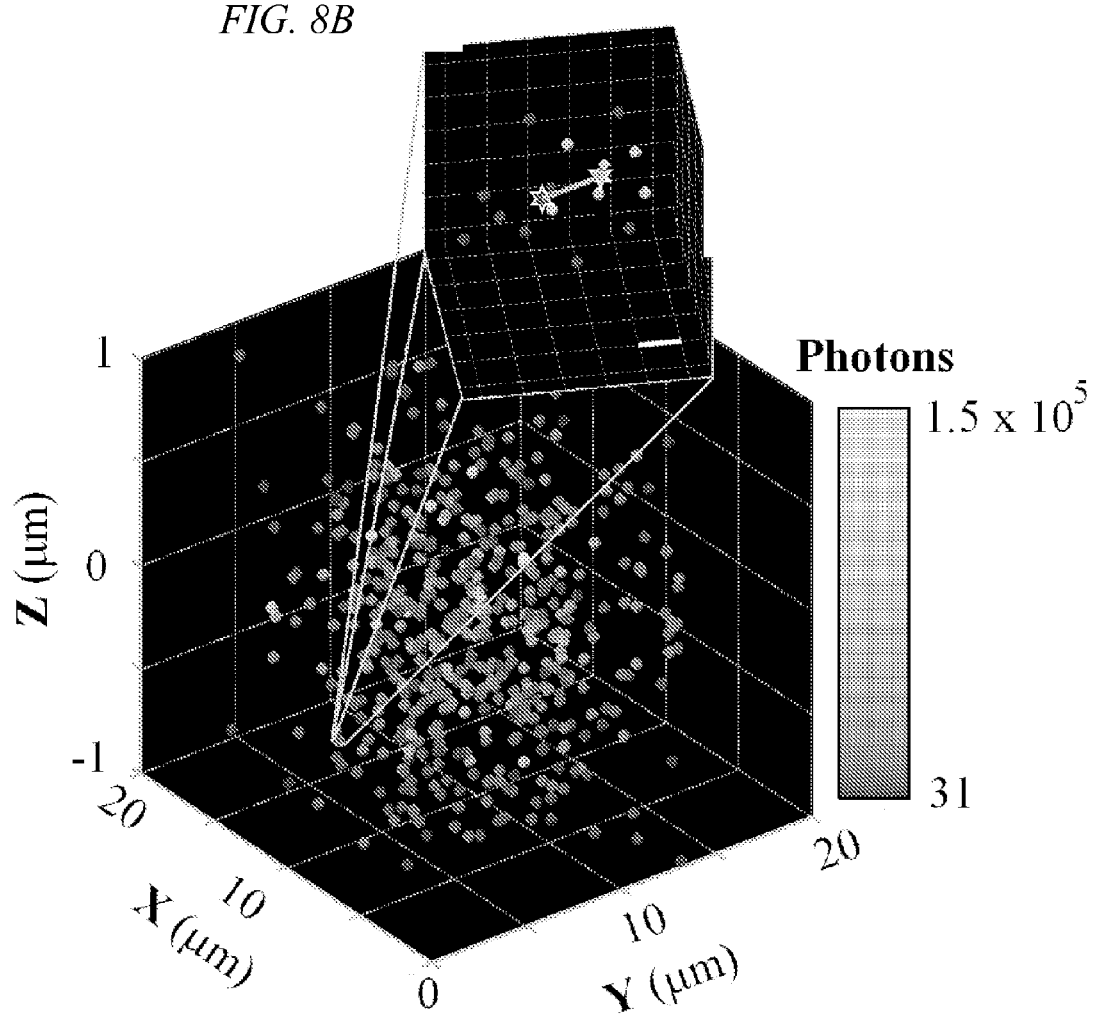
*FIG. 8B*
*FIG. 8A*
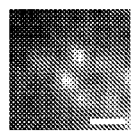
*FIG. 8C*
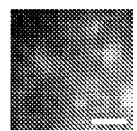
*FIG. 8D*
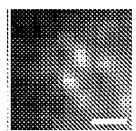
*FIG. 8E*

THREE-DIMENSIONAL SINGLE-MOLECULE FLUORESCENCE IMAGING BEYOND THE DIFFRACTION LIMIT USING A DOUBLE-HELIX POINT SPREAD FUNCTION

CROSS REFERENCE TO RELATED APPLICATIONS

This application claims the benefit of commonly assigned U.S. Provisional Patent Application No. 61/138,462, filed Dec. 17, 2008, entitled "Three-Dimensional Single-Molecule Fluorescence Imaging Beyond the Diffraction Limit Using A Double-Helix Point Spread Function," the disclosure of which is herein incorporated by reference for all purposes.

FEDERALLY SPONSORED RESEARCH AND DEVELOPMENT

This invention was made with Government support under contract HG003638 and GM085437 awarded by the National Institutes of Health. This invention was made with government support under grant number DMI0304650 awarded by the National Science Foundation. The Government may have certain rights in this invention.

BACKGROUND

Fluorescence microscopy is ubiquitous in biological studies because light can noninvasively probe the interior of a cell with high signal-to-background and remarkable label specificity. Unfortunately, optical diffraction limits the transverse (x-y) resolution of a conventional fluorescence microscope to approximately $\lambda/(2NA)$, where $\lambda$ is the optical wavelength and NA is the numerical aperture of the objective lens. This limitation may require that point sources need be more than about 200 nm apart in the visible wavelength region in order to be resolved with modern high-quality fluorescence microscopes. Diffraction causes the image of a single point emitter to appear as a blob (i.e., the point-spread function) with a width given by the diffraction limit. However, if the shape of the point spread function is measured, then the center position of the blob can be determined with a far greater precision (termed super-localization) that scales approximately as the diffraction limit divided by the square root of the number of photons collected, a fact noted as early as Heisenberg in the context of electron localization with photons and later extended to point objects and single-molecule emitters. Because single-molecule emitters are only a few nm in size, they represent particularly useful point sources for imaging, and super-localization of single molecules at room temperature has been pushed to the one nanometer regime in transverse (two-dimensional) imaging. In the third (z) dimension, diffraction also limits resolution to $\sim 2\ n\lambda/NA^2$ with n the index of refraction, corresponding to a depth of field of about 500 nm in the visible with modern microscopes. Improvements in three-dimensional localization beyond this limit are also possible using astigmatism, defocusing, or simultaneous multiplane viewing.

Until recently, super-localization of individual molecules was unable to provide true resolution beyond the diffraction limit (super-resolution) because the concentration of emitters had to be kept at a very low value, less than one molecule every $(200\ nm)^2$, to prevent overlap of the point spread functions. In 2006, three groups independently proposed localizing sparse ensembles of photoswitchable or photoactivatable molecules as a solution to the "high concentration problem" to obtain super-resolution fluorescence images (denoted PALM, STORM, F-PALM, respectively). A final image is formed by summing the locations of all single molecules derived from sequential imaging of the separate randomly generated sparse collections. Variations on this idea have also appeared, for example, by using accumulated binding of diffusible probes, molecules whose emission blinks on and off, or quantum dot blinking Several of these techniques have recently been pushed to three dimensions using astigmatism, interfering multiple beams, and/or multiplane methods to quantify the z-position of the emitters. In the astigmatic case, the depth of field was only about 600 nm, whereas in the extensively analyzed multiplane approach, the maximum depth of field was about 1 µm. In the case of multiple beam interference, the optical configuration is complex and requires extreme stability.

BRIEF SUMMARY

Embodiments of the present invention can resolve molecules beyond the optical diffraction limit. In some embodiments, a double-helix point spread function can be used to in conjunction with standard microscope optics to provide dual-lobed images of a molecule. Based on the rotation of the dual-lobed image, the axial position of the molecule can be estimated or determined. In some embodiments, the angular rotation of the dual-lobed imaged can be determined using a centroid calculation or by fitting the two lobes. Regardless of the technique, the correspondence between the shape of the rotating double-helix point spread function and axial position can be utilized. In some embodiments the axial position can be determined based on an angular rotation of the double-helix point spread function, which can be determined by finding the transverse position of features (e.g., lobes) of the double-helix point spread function.

Some embodiments of the invention can be utilized with wide field fluorescence imaging devices. For instance, an imaging system can include a microscope that images a sample at or near an objective focal plane and followed by any type of secondary imaging system. Between the microscope and the secondary imaging system a phase-mask can be placed that generates a double-helix point spread function. In particular the phase-mask can be implemented with a spatial light modulator placed in the Fourier plane of the microscope or any other appropriate plane. Various other lens, filters, polarizers, and/or other optical elements can also be implemented.

BRIEF DESCRIPTION OF THE DRAWINGS

FIG. 3A shows the structure of a single DCDHF-P molecule according to one embodiment.

FIG. 3B shows the localization precision as a function of the number of photons used in the fitting algorithm for the x direction using acquisition times of 500 ms and the rms background noise in the samples was approximately 20 photons/pixel according to one embodiment.

FIG. 3C shows the localization precision as a function of the number of photons used in the fitting algorithm for the y direction using acquisition times of 500 ms and the rms background noise in the samples was approximately 20 photons/pixel according to one embodiment.

FIG. 3D shows the localization precision as a function of the number of photons used in the fitting algorithm for the z direction using acquisition times of 500 ms and the rms background noise in the samples was approximately 20 photons/pixel according to one embodiment.

FIG. 4B shows 4-Azido-2,3,5,6-tetrafluorobenzaldehyde, according to one embodiment.

FIG. 8A shows 3D superresolution localization of high concentrations of single molecules of $DCDHF-V-PF_4$-azide in a thick PMMA sample, using the PALM/STORM/F-PALM method, according to one embodiment of the invention.

FIG. 8B shows a zoom in of position estimations for molecules 1 and 2 (blue and red, respectively) separated by 14 nm (X), 26 nm (Y), and 21 nm (Z); Euclidean distance (green): 36 nm, according to one embodiment of the invention.

FIG. 8C shows activation 1 showing molecule 1 according to one embodiment of the invention.

FIG. 8D shows activation 2 confirming that molecule 1 bleached, according to one embodiment of the invention.

FIG. 8E shows activation 3 showing molecule 2 according to one embodiment of the invention.

DETAILED DESCRIPTION

Point Spread Function Engineering

Figure 1A:
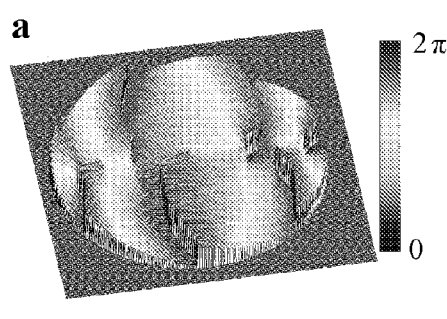
FIG. 1A shows a double-helix point spread function phase mask exhibiting 7 phase singularities according to one embodiment.

The double-helix point spread function exhibits two prominent lobes that rotate with axial position. This point spread function can be related to a class of propagation-invariant rotating beams, which can be obtained by superposing optical modes that fall along a line in the Gauss-Laguerre (GL) modal plane. Because an exact line-superposition results in an extremely absorptive and lossy mask, an iterative optimization procedure operating in three different domains can be used to design a photon-efficient double-helix point spread function phase mask. These three domains can include the GL modal plane, the Fourier plane, and the spatial plane. Such a point spread function is shown, for example, in FIG. 1A.

Figure 1B:
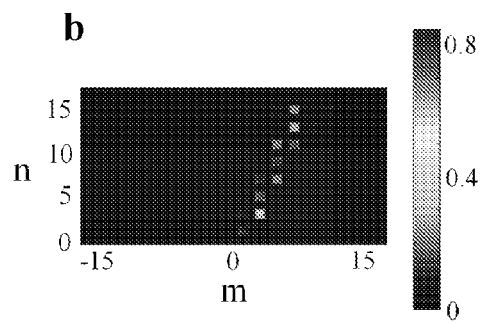
FIG. 1B shows the Gauss Laguerre (GL) modes constituting the mask forming a cloud in the GL modal plane with (m, n) as the indices of the GL modes according to one embodiment.

In some embodiments, a point spread function may be designed to optimize a phase-only transfer function generated with an on-axis double-helix point spread function, whose two lobes exhibit, for example, not more than a 180° rotation along the focal region, while carrying maximum point spread function energy in them. With an understanding of the significance of the phase of GL modes over their amplitude, the design procedure expanded the degrees of freedom in the GL modal plane (for example, see FIG. 1B) to simultaneously satisfy all of the above constraints. This resulted in a double-helix point spread function phase mask with over 30 times higher transfer-function efficiency compared to the perfectly propagation-invariant superposition, thereby enabling the use of the double-helix point spread function in photon-limited applications.

In some embodiments, a double-helix point spread function can be created with a phase mask or a diffractive optical element. For example, the point spread function can be created by superposing optical modes that fall along a line in the Gauss-Laguerre (GL) modal plane. These elements can be fabricated by electron beam lithography, proportional reactive ion etching in $SiO_2$, hot embossing in PMMA, gray level lithography, direct laser writing, etc.

Gaussian Estimation Scheme

Figure 2A:
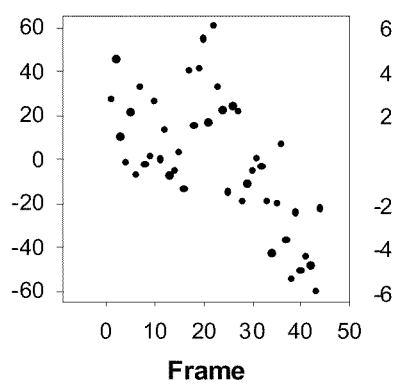
FIG. 2A shows estimations of the z position of the DCDHF-V-PF$_4$ molecule shown in FIG. 6A according to one embodiment.
Figure 2B:
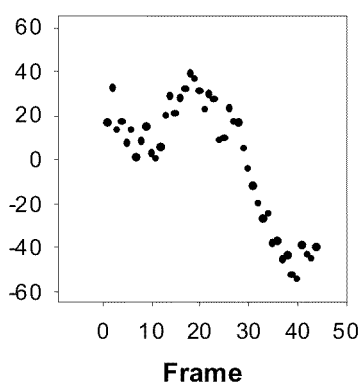
FIG. 2B shows estimations of the z position of the fluorescent bead fiduciary in the sample, illustrating the z drift of the microscope and/or the z-piezo according to one embodiment.
Figure 2C:
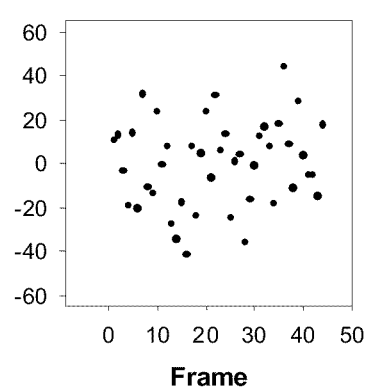
FIG. 2C shows a fiduciary-corrected positions of the single molecule according to one embodiment.

In some embodiments, a nonlinear fitting algorithm was developed for the molecule shown in FIGS. 2A, 2B and 2C. This fitting algorithm, for example, provides better localization precision than centroid estimation with the double-helix point spread function system. Each lobe was identified and can be isolated within, for instance, a (x-pixel)$^2$ window, where x can be any integer; for example, any integer between 6 and 25. The lobes in the point spread function were then each fit to a 2-D Gaussian using, for example, an nlinfit function, to extract an estimate of the center position of each lobe. Then the standard double-helix point spread function procedure for finding the x, y, and z positions of the molecule can be performed using the angle of the line between the two lobe positions to extract z, and the midpoint to extract x and y. This fitting procedure can give better results than a simple centroid computation fit, although it can be significantly more complex computationally. For a typical molecule it offers a 15% improvement in localization precision in all three directions over the cruder centroid fit algorithm. For the large number of single molecules in FIGS. 7 and 8, under some conditions a centroid fitting scheme may be used both because the improvement is not overly significant for most molecules and because the centroid calculation takes up less computational time. Such computations can be calculated using, for example, the computational device shown in FIG. 10.

In addition, for the data in FIGS. 2A, 2B and 2C, a 100 nm fluorescent bead (Fluospheres 565/580, Molecular Probes, Inc.) was used a fiduciary marker. Because the bead emits many more photons, its localization precision is much better than for a single molecule. FIGS. 2A, 2B and 2C show the position fluctuations of the bead (FIG. 2B) and the molecule (FIG. 2A), and the dramatic improvement in z estimation drift (FIG. 2C) that results from subtracting the bead motion from the single-molecule z-estimations.

Estimation Algorithm for 3-D Images

Figure 10:
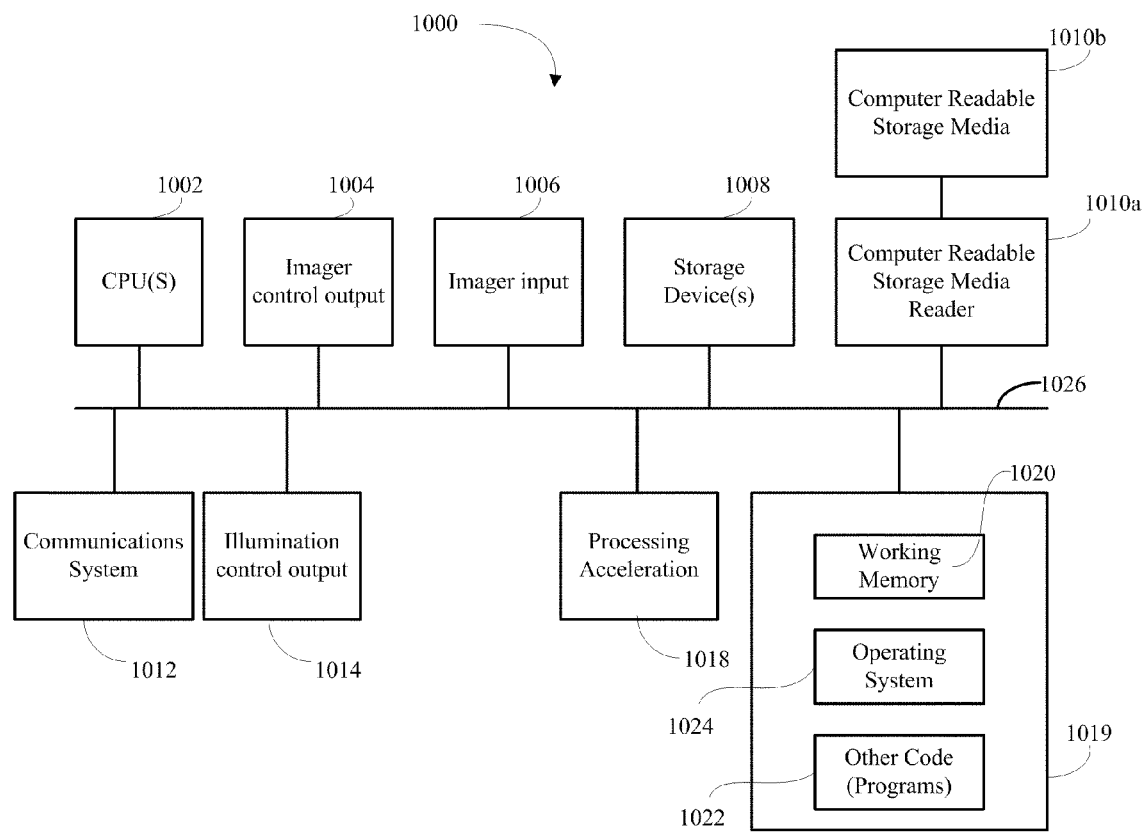
FIG. 10 shows a block diagram of a computational device that can be used to determine dimension from images of a molecule according to some embodiments.

Each frame of the raw detected movies shows multiple molecules located over a transverse-position-dependent background that resembles the Gaussian intensity profile of the excitation beam. 3D positions of the molecules in each of these frames are estimated with an algorithm implemented, for example, using the processor shown in FIG. 10. The algorithm first finds the coarse molecule positions from the raw image, and then zooms in on these coarse positions to find the exact 3D positions as explained below.

The non-uniform background prohibits the use of direct thresholding to identify molecules in the raw detected image. An edge detection algorithm can be used to calculate the modulo-square of the gradient of the raw image to locate the coarse molecule positions. The gradient distinguishes the molecules from the slowly varying background by highlighting the edges around the molecules' response. The centroid of the area enclosed by the edges of a molecule is taken as the molecule's coarse x and y position. For example, a (19 pixel)$^2$ region centered about the coarse position is then extracted out to find the exact 3D molecule position. The two double-helix point spread function lobes present within this region are separated from the background using an adaptive thresholding technique. This technique finds the smallest threshold above the background such that the areas of the two lobes are maximized while remaining disconnected. The photon counts used for the colormap of FIG. 7C and in the horizontal axis of FIGS. 3B, 3C and 3D are the photons counted from these maximum lobe-areas after background correction. The centroid coordinates of the two double-helix point spread function lobes were then computed. The axial position of the molecule was estimated by mapping the angle between the two centroid locations to axial distance using the calibration plot shown in FIG. 5B. The transverse molecule positions were estimated from the midpoint of the centroids of the double-helix point spread function lobes after applying a z-dependent transverse correction. This correction compensates for a small systematic change in transverse position of the double-helix point spread function lobe centroid midpoint as a function of z, determined from fluorescent bead imaging with z-focus displacement produced by a piezoelectric mount for the microscope objective.

This estimation algorithm finally generated a 4D (3D spatial-temporal) dataset containing the molecule positions from different camera frames. This matrix was directly displayed in FIG. 7C. In FIG. 8, the temporal dimension, for example, was squeezed by replacing multiple localizations of a molecule within an activation cycle with the mean estimate. The precisions shown in the vertical axis of FIGS. 3B, 3C and 3D are the standard deviations of estimates of the position for multiple molecules obtained from the above 4D dataset after a drift correction based on correlation analysis of the single-molecule positions, which compensated for any linear stage drift along any of the three dimensions. This approach was utilized since it can be difficult to have multiple non-saturated fiduciary beads available for fiduciary position corrections in this case.

Localization Precision as a Function of the Number of Detected Photons

FIGS. 3B, 3C and 3D show plots of the localization precision for multiple localizations of different DCDHF-P molecules versus the number of photons used in the fitting algorithm for that molecule. The ordinate of each plot refers to the localization precision as defined by the standard deviation of the population of molecule location measurements as illustrated in FIG. 2A, which can be regarded as the localization precision expected for a single position determination. Our estimation algorithm does not use all of the photons in the double-helix point spread function, but rather applies an adaptive threshold that only uses photons in the primary two lobes above a certain background level as described above. There can be a weak and seemingly linear negative correlation between the localization precision and number of photons, but a full analysis of this and the development of an optimal estimation algorithm are subjects of future work. A possible reason for the scatter is that the double-helix point spread function shape can change slightly depending on the axial position of the emitter, that is, one lobe appears better defined than the other at certain axial positions, possibly arising from aberration effects. Another reason is that the background fluctuations from position to position are partly deterministic: because much of the background itself is actually weak, the sidelobes from the various GL modes forming the point spread function combine to make a widely spatially varying, but temporally constant, variation across the sample.

Calibration of CCD Gain for Photon Counting

In some embodiments, in order to convert EMCCD camera counts to photons, two calibrations may be required: the conversion gain, (number of e⁻ after on-chip gain)/(ADC count), and the electron multiplication gain (number of e⁻ after on-chip gain)/(number of photoelectrons). The conversion gain was calibrated according to procedures known in the art. In some embodiments, the method proceeds as follows. First, one records two images of a dim uniform field (a blank, clean coverslip) at the same light intensity level with no EM gain for an arbitrary number of evenly spaced intensities. Due to Poisson fluctuations in detected photons, a plot of the variance of the image for each intensity level versus the mean signal of the image for each intensity level may be a straight line with a slope that equals the inverse of the conversion gain. Significant flat-field effects due to nonuniformity in pixel sensitivity caused a nonlinear dependence and they were removed by methods known in the art.

The electron multiplication gain on the camera needs to be calibrated because the value selected in the software does not always exactly match the true value. To calculate this factor for any software input value, we measured the ratio of the mean signal under an arbitrary irradiance and the mean signal with the camera shutter closed. Because dark counts are negligible, the electron multiplication gain is then determined by computing this ratio with the gain on divided by this ratio with the gain off (i.e., multiplicative gain=1).

Synthesis of Photoactivatable Fluorophore DCDHF-V-PF$_4$-azide

Any type of photoactivatble fluorescing material or molecule whose fluorescence blinks on and off can be used in embodiments of the invention. The following molecules are intended as examples only.

Figure 4A:
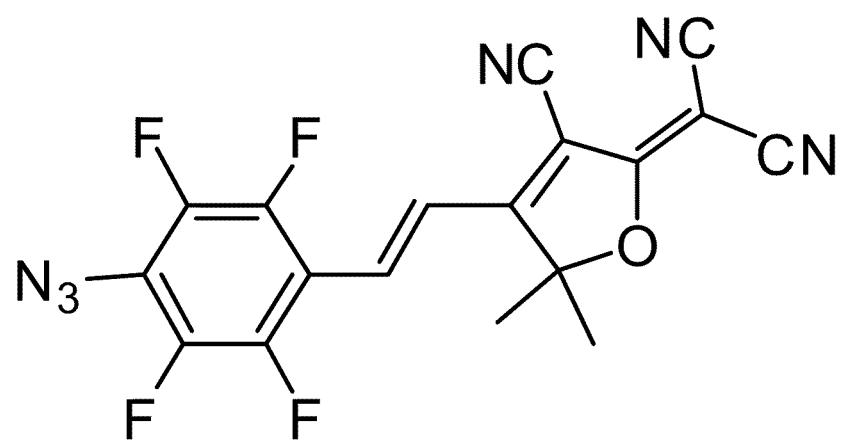
FIG. 4A shows 4-Azido-2,3,5,6-tetrafluorobenzaldehyde, according to one embodiment.
Figure 4B:
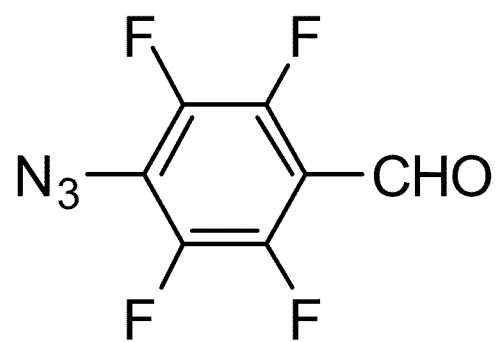
FIG. 4B shows a molecule of 4-(4-Azido-2,3,5,6-tetrafluorostyryl)-3-cyano-5,5-dimethylfuran-2 (5H)-ylidene)malononitrile ($DCDHF-V-PF_4$-azide), according to one embodiment.

FIG. 4B shows 4-Azido-2,3,5,6-tetrafluorobenzaldehyde, according to one embodiment. This molecule was created, for example, by adding pentafluorobenzaldehyde (1.96 g, 0.01 mol), sodium azide (0.72 g, 0.011 mol), acetone (15 mL) and water (15 mL) to a 100-mL round-bottom flask with stirbar. The mixture was warmed to reflux under nitrogen for 10 h. TLC showed all the pentafluorobenzaldehyde was consumed and so the reaction was stopped and cooled to room temperature. The product mixture was diluted with 20 mL of water. The crude product was extracted with ether (30 mL×5). The combined organic layer was dried over anhydrous MgSO$_4$. The solvent was removed at room temperature under vacuum. Sublimation of the residue (50° C./0.2 mm) gave the final product as a white solid (1.20 g, 55% yield). Mp 44° C. (lit 44-45° C.). IR (neat): 3377, 2121, 1704, 1644, 1480, 1398, 1237, 1066, 1000, 615 cm$^{-1}$. $^1$H NMR (400 MHz, CDCl$_3$): δ 10.26 (m, 1H); $^{19}$F NMR (470 MHz, CDCl$_3$): δ −149.6 (m, 2F), −155.6 (m, 2F).

FIG. 4A shows a molecule of 4-(4-Azido-2,3,5,6-tetrafluorostyryl)-3-cyano-5,5-dimethylfuran-2 (5H)-ylidene)malononitrile (DCDHF-V-PF4-azide), according to one embodiment. This molecule was created, for example, by adding 4-azido-2,3,5,6-tetrafluorobenzaldehyde (0.22 g, 1 mmol) and 2-(3-cyano-4,5,5-trimethyl-5H-furan-2-ylidene)-malononitrile (0.22 g, 1.1 mmol), 5 mL pyridine and several drops of acetic acid to a 100-mL round-bottom flask with stirbar. The mixture was stirred at room temperature for 2.5 days. TLC showed the desired azido product had been formed as the main product. The reaction was stopped and poured into 500 mL ice-water. After stirring for 2 h, the precipitate was filtered off by suction filtration. The solid was recrystallized from 1-propanol. After recrystallization, part of the azido product was converted to the corresponding amino compound. The mixture was adsorbed on silica gel, placed at the top of a silica column and eluted (CH$_2$Cl$_2$:EtOAc=20:1). Fractions containing only the first product were combined and concentrated to give an orange product (40 mg, 10% yield). This can be the final azido product, (E)-2-(4-(4-azido-2,3,5,6-tetrafluorostyryl)-3-cyano-5,5-dimethylfuran-2 (5H)-ylidene)malononitrile. Recrystallization could not be done on this compound, since it has high photoreactivity: it readily converts to the corresponding amino compound in solvents (like propanol) in daylight. IR (neat): 2933, 2228, 2124, 1586, 1557, 1489, 1372, 1253, 998 cm$^{-1}$. $^1$H NMR (400 MHz, CDCl$_3$): δ 7.63 (d, J=16.8 Hz, 1H), 7.31 (d, J=16.4 Hz, 1H), 1.82 (s, 6H); $^{13}$C NMR (100 MHz, CDCl$_3$): δ 174.5, 172.5, 146.9 (m), 144.4 (m), 142.0 (m), 139.4 (m), 130.7, 121.4 (t, J=9.8 Hz), 111.1, 110.3, 109.5, 102.6, 97.8, 51.3, 26.3; $^{19}$F NMR (470 MHz, CDCl$_3$): δ −143.5 (2F), −155.2 (2F). UV-vis (EtOH): $\lambda_{max}$=406 nm, $\epsilon$=2.7×10$^4$ L mol$^{-1}$ cm$^{-1}$.

Methods for Using a Double-Helix Point Spread Function to Determine Molecular Position In some embodiments, a new method for three-dimensional super-resolution imaging is disclosed with single fluorescent molecules where the point spread function of the microscope has been engineered to have two lobes that have a different angle between them depending on the axial position of the emitting molecule. In effect, the point spread function appears as a double-helix along the z-axis of the microscope, thus we term it the double-helix point spread function for convenience, see FIG. 5D. Rotating intensity double-helix point spread function distributions may be formed by taking superpositions of Gauss-Laguerre (GL) modes that form a cloud along a line in the GL modal plane. The double-helix point spread function has been used to localize photon-unlimited point scatterers inside the volume of a glass slide, and to track moving fluorescent microspheres. In addition, an information theoretical analysis shows that the double-helix point spread function can provide higher and more uniform Fisher information for three-dimensional (3D) position estimation than the point spread functions of conventional lenses.

A particularly useful photon-limited source, a single-molecule emission dipole, for example, can be imaged far beyond the diffraction limit using a double-helix point spread function. In thick samples, super-localization of single fluorescent molecules with precisions as low as 10 nm laterally and 20 nm axially over axial ranges of greater than 2 μm can be obtained. Further, a three-dimensional superresolution imaging of high concentrations of single molecules in a bulk polymer sample can be achieved in one embodiment using a new photoactivatable 2-dicyanomethylene-3-cyano-2,5-dihydrofuran (DCDHF) fluorophore, a modification of the recently reported azido-DCDHF. Two molecules as close as 14 nm (x), 26 nm (y), and 21 nm (z) are resolved by this technique. The ideas presented here should be broadly applicable to super-resolution imaging in various fields ranging from single emitters in solid hosts for materials science applications to biological and biomedical imaging studies.

Fundamentals of Imaging Using the Double-Helix Point Spread Function

Figure 5A:
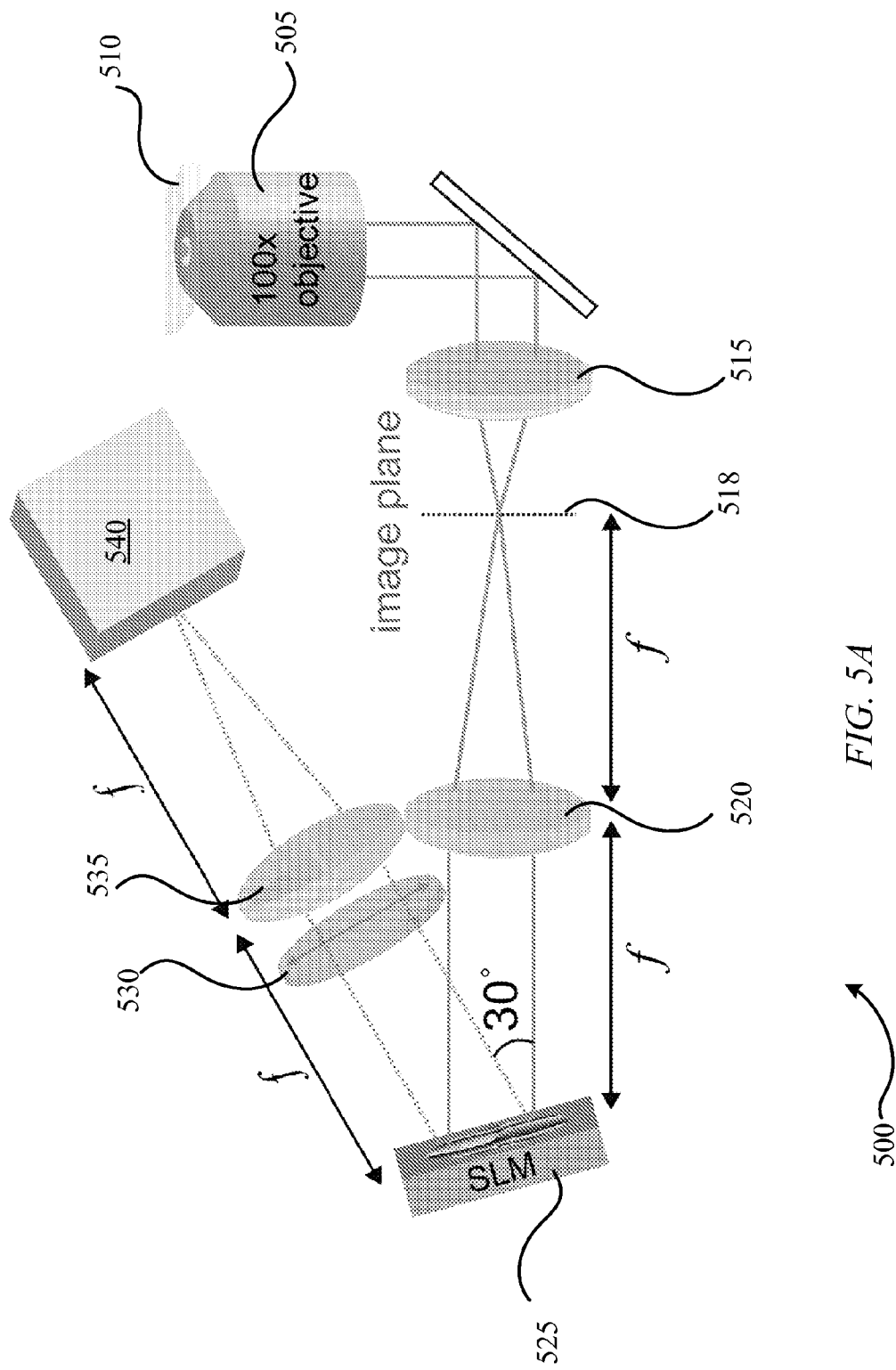
FIG. 5A shows a collection path of the single-molecule double-helix point spread function setup according to one embodiment.
Figure 5B:
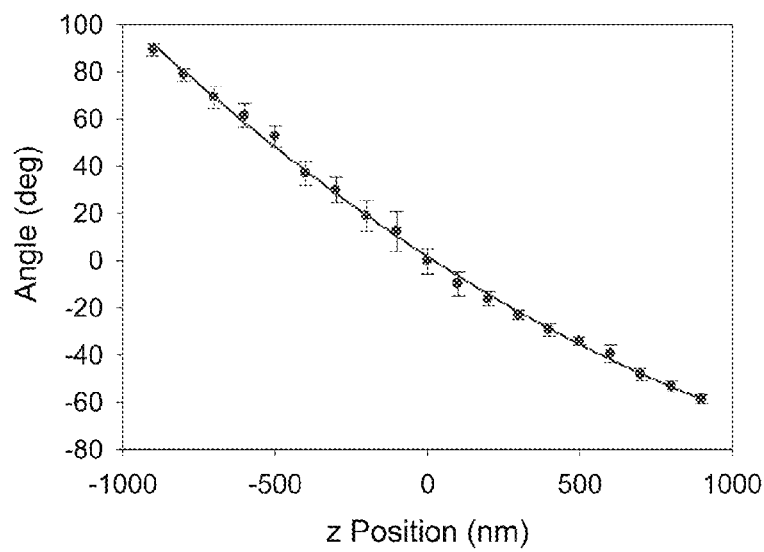
FIG. 5B shows a typical calibration curve of angle between two lobes with respect to the horizontal versus axial position measured with a piezo-controlled objective.

In some embodiments, the 3D positions of multiple sparse molecules are estimated with a single wide-field fluorescence image using the double-helix point spread function design as shown in FIG. 5A. Imaging system 500, for example, can be composed of a sample located at the objective focal plane 510 of microscope objective 505 and tube lens 515 with image plane 518 (e.g. a conventional microscope) and an optical signal processing section. The signal processing section can be essentially a 4f imaging system with a reflective phase-only spatial light modulator placed in the Fourier plane. Specifically, an achromatic lens 515 can be placed at a distance f from the microscope's image plane 518 produces the Fourier transform of the image at a distance f behind the lens. The phase of the Fourier transform can be modulated by reflection from the liquid crystal spatial light modulator 525. The spatial light modulator can include a double-helix point spread function. Because spatial light modulator 525 can be sensitive only to vertically polarized light, a vertical polarizer 530 can be placed immediately after spatial light modulator 525 to block any horizontally polarized light not modulated by spatial light modulator 525. The final image can be produced by another achromatic lens 535 (e.g., f=15 cm) placed at a distance f after spatial light modulator 525 and recorded with camera 540 (e.g., a EMCCD camera).

Figure 5C:
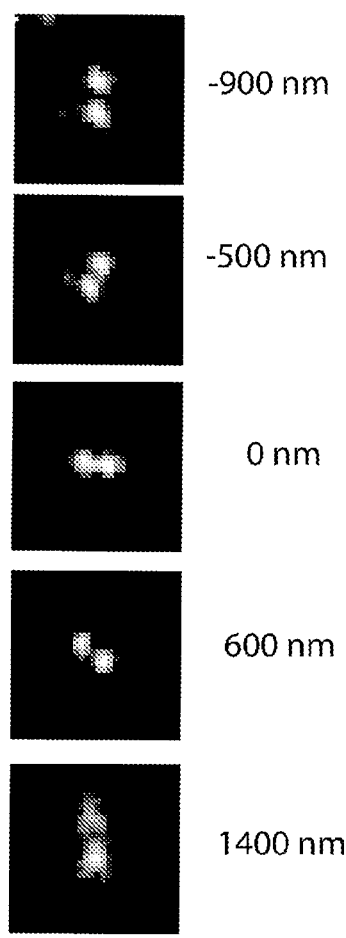
FIG. 5C shows double-helix point spread function images from a single fluorescent bead used for the calibration curve at different axial positions, with 0 being in focus according to one embodiment.
Figure 5D:
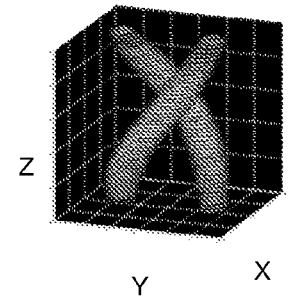
FIG. 5D shows a 3D plot of the double-helix point spread function intensity profile according to one embodiment.

When spatial light modulator 525 is loaded with the double-helix point spread function phase-mask, the Fourier transform of the sample image can be multiplied by the double-helix point spread function transfer function. Equivalently, every object point may be convolved with two lobes, with the angular orientation of the lobes depending on the axial location of the object above or below focus. The lobes may be horizontal when the emitter is in focus. As the emitter is moved towards the objective, the double-helix point spread function lobes may rotate in the counter-clockwise direction. On the other hand, if the emitter is moved away from the objective the lobes may rotate in the clockwise direction. When a sample comprises multiple sparse molecules at different 3D positions, the detected double-helix point spread function image may exhibit two lobes (with different angular orientations) for each molecule. The transverse (x-y) position of a molecule may be estimated from the midpoint of the line connecting the positions of the two lobes, and the axial position can be estimated from the angle of the line connecting the two lobes using a calibration plot that maps angles to axial positions. An example calibration plot of angle versus z position is shown FIG. 5B. FIG. 5D is a simulation of the three dimensional shape of the double-helix point spread function. FIG. 5C also shows actual double-helix point spread function images taken from a fluorescent bead at different z positions illustrating the type of data used to extract the calibration plot. The beads (pumped with 514 nm) have an emission spectrum with a peak at about 580 nm.

Single-Molecule Localization Using the Double-Helix Point Spread Function

Figure 6A:
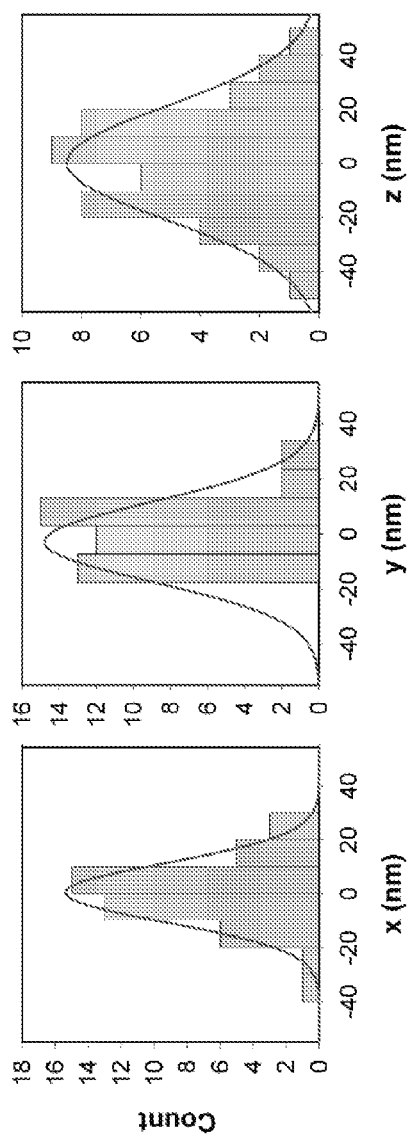
FIG. 6A shows a histogram of 44 localizations of one single photoactivated $DCDHF-V-PF_4$ molecule in x, y, and z in a layer of PMMA, according to one embodiment. The standard deviations of the measurements in x, y, and z are 12.8, 12.1, and 19.5 nm, respectively. The smooth curve is a Gaussian fit in each case. An average of 9300 photons were detected per estimation on top of background noise fluctuations of 48 photons/pixel.
Figure 6C:
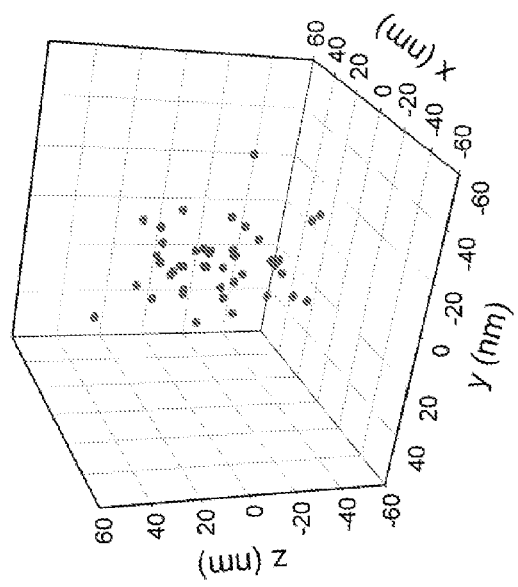
FIG. 6C shows localizations of a single molecule plotted in three dimensions according to one embodiment of the invention.
Figure 6B:
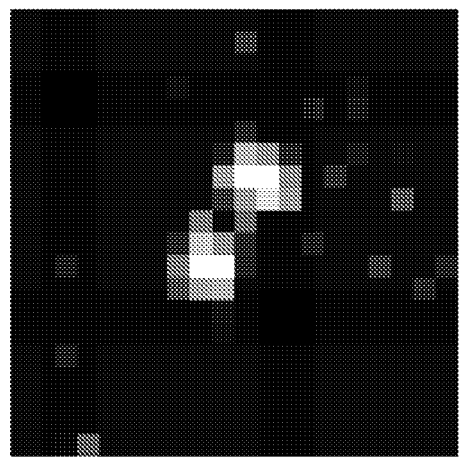
FIG. 6B shows a representative single-molecule image with double-helix point spread function acquired in one 500-ms frame according to one embodiment of the invention.

Imaging of single molecules can be difficult because of the much lower signal-to-background inherent in a typical single-molecule experiment. Single-molecule imaging can be impeded by the >75% loss associated with the spatial light modulator reflection arising from non-idealities in the device. Nevertheless, we have achieved 3D localization precision that compares well with previous approaches while more than doubling the available depth of field. FIGS. 6A, 6B and 6C show the results from the localization of one single molecule in a 2 µm thick poly(methyl methacrylate) (PMMA) film. In this embodiment, the molecule can be a derivative of the previously described class of photoswitchable fluorogenic azido-DCDHF molecules, specifically (E)-2-(4-(4-Azido-2,3,5,6-tetrafluorostyryl)-3-cyano-5,5-dimethylfuran-2 (5H)-ylidene) malononitrile, abbreviated as $DCDHF-V-PF_4$-azide. For the data shown, the fluorogenic azide functionalized molecule was previously irradiated with 407 nm light to generate the amine functionalized emissive form. For imaging, the molecule was pumped with 514 nm and the fluorescence peaking at 580 nm was recorded for 500 ms/frame to yield images shown in FIG. 6B.

In some embodiments, the double-helix point spread function of a single molecule may be fit using any of a number of different schemes. A first method can find the center of each lobe using a least-squares Gaussian fit, then determine the midpoint between the centers of the Gaussians to define the x,y position of the bead, and finally obtain the angle between the centers of the two Gaussians relative to a reference line, which gives the z position of the emitter. Another method, which can be more computationally efficient than the first, fits the lobes of the point spread function using a simple centroid calculation. The first procedure gives better precision measurements than the second, although it is less robust in that it may require a fairly symmetric shape to obtain a good fit. Another method can include methods of statistical inference such as the maximum likelihood method. In yet another embodiment, the point of maximum intensity of a lobe as found within an image can be used rather than the center of the lobe. From the point of maximum intensity of the two lobes, an angular rotation can be determined. The data in FIGS. 6A, 6B and 6C was analyzed using the first scheme, and data for the large number of molecules in FIGS. 7A, 7B, 7C, 8A, 8B, 8C, 8D, and 8E was analyzed using the second scheme for computational convenience.

Experiments have been performed using embodiments of the invention and a three-dimensional position of one single molecule was estimated 44 times and the histograms of the three spatial coordinates of the molecule are presented in FIG. 6A. The molecule was found to have a mean z position of 644 nm above the standard focal plane. Each estimation used an average of 9300 photons with an average rms background fluctuation of 48 photons per pixel. The histograms in FIG. 6A may be regarded as a population of successive position determinations which have a population standard deviation, or localization precision, of 12.8, 12.1, and 19.5 nm in x, y, and z, respectively. These values should be regarded as the expected localization precision for a single measurement. As is well-known, if all the 44 position measurements in FIGS. 5A, 5B, 5C and 5D are combined, the result will have a far smaller localization precision as would be expected from the scaling of the standard error of the mean (i.e., the inverse of the square root of the number or measurements or 6.6 times smaller), but in many studies, multiple localizations of the same single molecule may not be possible. The localization precision of our method is within the same range as both the astigmatic and multiplane techniques, while simultaneously more than doubling the depth of field.

Figure 7A:
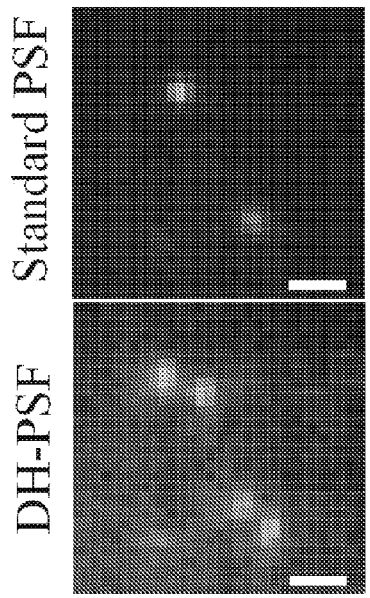
FIG. 7A shows a comparison of a standard point spread function (i.e., spatial light modulator off, upper panel) to the double-helix point spread function image of two molecules (lower panel, spatial light modulator on) according to one embodiment of the invention.
Figure 7B:
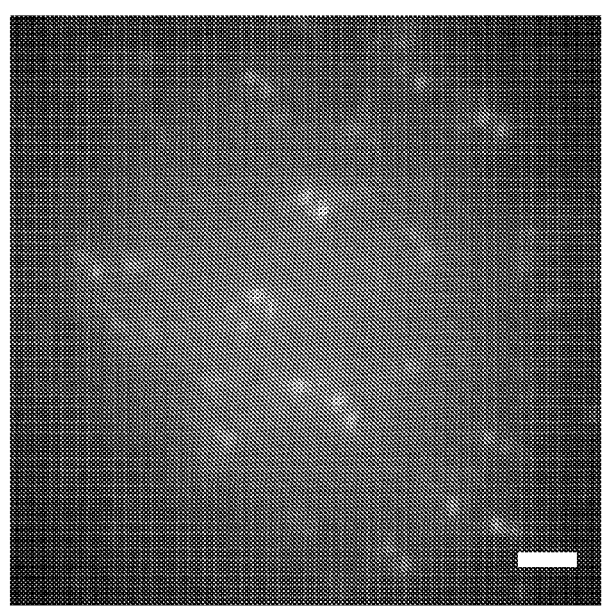
FIG. 7B shows a representative image of many single molecules at different x, y, z positions according to one embodiment of the invention.
Figure 7C:
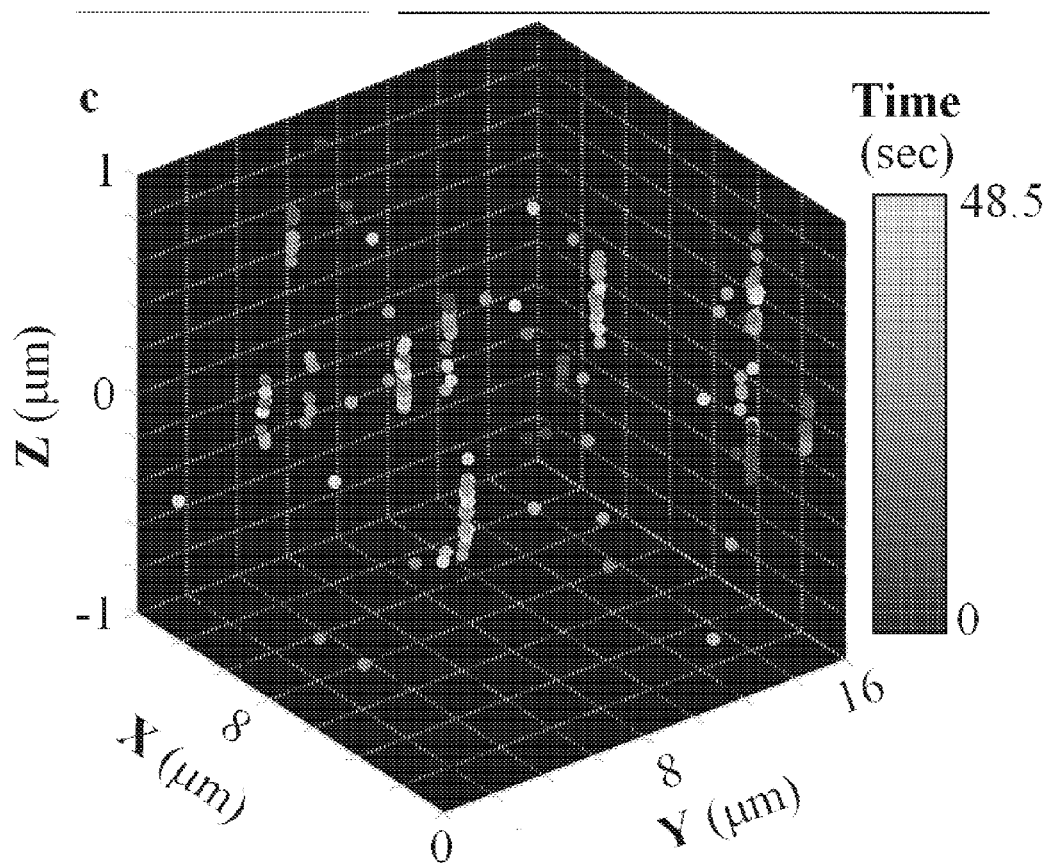
FIG. 7C shows a 4D (x, y, z, time) representation of single-molecule position determinations during a sequence of 97 frames, with a colormap showing the time of acquisition according to one embodiment of the invention.

Double-Helix Point Spread Function Imaging of Single Molecules in a Thick Sample The double-helix point spread function imaging system can be used to identify the 3D position of many molecules in a single image as long as the point spread functions from the different emitters do not appreciably overlap. FIGS. 7A, 7B and/or 7C demonstrates this capability using a sample containing a low concentration of the fluorophore DCDHF-P embedded in a 2 µm thick PMMA film. FIG. 7A compares the standard and the double-helix point spread function images of two molecules at different 3D positions selected to be fairly close to the focal plane for purposes of illustration only. Notable in the double-helix point spread function image is a slightly increased background compared to the standard point spread function, a property which arises from the distribution of photons between the double-helix point spread function lobes over a long axial range. In general, molecules away from the focal plane appear quite blurry in the standard point spread function image. In contrast, the double-helix point spread function image encodes the axial position of the molecules in the angular orientation of the molecules' double-helix point spread function lobes, which are distinctly above the background with approximately the same intensity through the entire z range of interest. This increased depth-of-field is illustrated in FIG. 7B, which shows a representative double-helix point spread function image of multiple molecules in a volume. Each molecule is seen to exhibit two lobes oriented at an angle that can be uniquely related to its axial position. This image can be obtained by averaging 97 successive frames recorded with a 500 ms exposure time. FIG. 7C shows the 3D positions of molecules extracted from each of these 97 frames as a function of time in the imaging sequence (encoded in the colormap). Molecules were localized below the diffraction limit over an axial range of 2 µm. Molecules that were localized more than once are shown as a group of points, each representing a single localization event. The apparent spread of these point is not due to drift, but is rather an ensemble of multiple position determinations as in FIG. 6A.

Imaging of Molecules Spaced Closer than the Diffraction Limit

When a large concentration of fluorophores is present, repeated photo-activation, image acquisition, localization, and photobleaching of fluorescent molecules provides resolutions beyond the classical diffraction limit (superresolution). FIG. 8 shows that three-dimensional superresolution can be achieved with a double-helix point spread function system. We used the fluorogenic DCDHF-V-PF$_4$-azide as our photoactivatable molecule, again in a thick film of PMMA. The molecules were photoactivated with 407 nm light, and then excited with 514 nm light to image the fluorescent emission centered at 578 nm. Accordingly, a double-helix point spread function mask designed for 578 nm was loaded into the spatial light modulator. The molecules were irradiated until photobleaching occurred. The power and the duration of the purple 407 nm beam were chosen so that only a sparse subset of molecules were activated in each cycle FIG. 8A shows the 3D extracted position of each molecule extracted from 30 activation cycles, with 30 (500 ms) frames per activation. The colormap encodes the total number of photons available for position localization. FIG. 8B shows a zoom-in of two molecules establishing the super-resolving capability of the method: these two molecules are separated by 14 nm (X), 26 nm (Y), and 21 nm (Z), for a Euclidean distance of 36 nm. FIGS. 8C-8E show the corresponding images for these two molecules through three consecutive activation cycles. Since these molecules are photoactivatable, but not photoswitchable, the molecules that appear in different imaging cycles (FIG. 8C and FIG. 8E) can be different molecules, because neither was present in the intervening cycle (FIG. 8D), and blinking of this fluorophore was minimal. As is known in the art, where photoactivatable, blinkable, or photoswitchable molecules are labeling a particular structure, super-resolution information can be extracted as long as the labeling density can be sufficiently high to satisfy the Nyquist criterion.

The double-helix point spread function provides a powerful new tool for 3D superlocalization and superresolution imaging of single molecules. By encoding the z-position in the angular orientation of two lobes in the image, the x, y, and z positions of each single emitter can be determined well beyond the optical diffraction limit. Moreover, the double-helix point spread function enables 3D imaging with greater depth of field than is available from other imaging methods. Despite losses from the insertion of a spatial light modulator into the imaging system, single small molecules can in fact be localized with precision in the 10-20 nm range in three dimensions with single images. In yet other embodiments, the precision can be between 5 nm and 50 nm. It is expected that future improvements in the phase mask design, the use of a custom phase mask, optimized estimators, background minimization, and a closed-loop drift correction will lead to even further improvements in resolution. With the proofs-of-principle reported here, the path is open to implementation of these ideas in a range of areas of science, including the study of materials for defect characterization, the quantum optical generation of novel optical fields using subwavelength localization of properly coupled single emitters, the use of single molecules to characterize nanostructures, and 3D biophysical and biomedical imaging of labeled biomolecules inside and outside of cells.

Sample Preparation

Axial position calibration data were obtained at two different emission wavelengths, 515 nm and 580 nm, using fluorescent beads (Fluospheres 505/515, 200 nm, biotin labeled, and Fluospheres 565/580, 100 nm, carboxylated, both from Molecular Probes) immobilized in a spin-coated layer of 1% poly(vinyl alcohol) (72000 g/mol, Carl Roth Chemicals) in water; the polymer solution was cleaned with activated charcoal and filtered before being doped with beads. Single-molecule samples were prepared by doping a nanomolar concentration of DCDHF-P into a 10% solution of poly(methyl methacrylate) ($T_g$=105° C., MW=75,000 g/mol atactic, polydispersity ~7.8, Polysciences, Inc.) in distilled toluene that was spun (at 2000 RPM for 30 s with an acceleration time of 10,000 RPM/s) onto a plasma-etched glass coverslip to form a ~2 µm thick layer. The thick photoactivatable sample was made similarly using the molecule DCDHF-V-PF$_4$-azide (synthesis in SI), except that a layer of PVA containing 656/580 nm fluorescent beads was spun on top of the PMMA layer to incorporate fiduciary markers in the images.

Imaging

According to one embodiment, epifluorescence images of both fluorescent beads and single molecules were collected with an Olympus IX71 inverted microscope equipped with a 1.4 NA 100× oil immersion objective, where the setup has been fully described previously with the exception of the collection path. The filters used were a dichroic mirror (Chroma Z514RDC or z488RDC) and a longpass filter (Omega XF3082 and Chroma HQ545LP). The objective was fitted with a z-piezo adjustable mount (PIFOC p-721.CDQ stage with E625.CO analog controller, Physik Instrumente) that allowed for control of the z-position of the objective. The samples were imaged with either 488 nm (DCDHF-P) or 514 nm (DCDHF-V-PF4-azide) circularly polarized excitation light (Coherent Innova 90 Ar$^+$ laser) with an irradiance of 1-10 kW/cm$^2$. Because some of the fluorogenic DCDHF-V-PF4-azide molecules were already activated, the molecules were first exposed to the 514 nm beam until most of them were bleached, leaving only a sparse subset of them in the fluorescent state. For further super-resolution imaging, molecules were photoactivated using circularly polarized 407 nm (Coherent Innova 300 Kr$^+$ laser) light with an irradiance of <1 kW/cm$^2$, which was chosen such that only a few molecules were turned on at a time. Images were then continuously acquired with 514 nm pumping with 500 ms exposure time. After all of the molecules were bleached, the green beam was blocked and the purple beam was unblocked for 100 ms to photo-activate additional molecules. The green beam was then unblocked for the next 15 seconds, until all of the activated molecules were bleached again. Each round of one 100-ms activation period and one 15-s imaging period constitutes one activation cycle. Thirty such cycles were required to obtain the data in FIG. 8. Mechanical shutters are used to control the timing of the imaging and activation beams.

In the collection path, a standard 4f imaging setup was utilized with a phase-only spatial light modulator (Boulder Nonlinear Systems XY Phase Series) programmed to generate the double-helix point spread function placed at the Fourier plane. The light exiting the sideport of the microscope was collected by a 15 cm focal length achromat lens (Edmund NT32-886) placed 15 cm from the microscope's image plane (25.5 cm from the exit port). The spatial light modulator was placed 15 cm from this lens at a slight angle such that the phase modulated reflected beam would be diverted from the incoming beam by ~30°. The phase pattern on the spatial light modulator was made using an optimization procedure described previously. The reflected light passed through a polarizer and was then collected by another achromat lens 15 cm from the spatial light modulator. The real image was then focused onto an EMCCD (Andor Ixon$^+$). Bead samples were imaged with no electron multiplication gain while single-molecule samples were imaged with a software gain setting of 250 yielding a calibrated gain of 224.5. The imaging acquisition rate for all single-molecule imaging was 2 Hz.

Process

Figure 9:
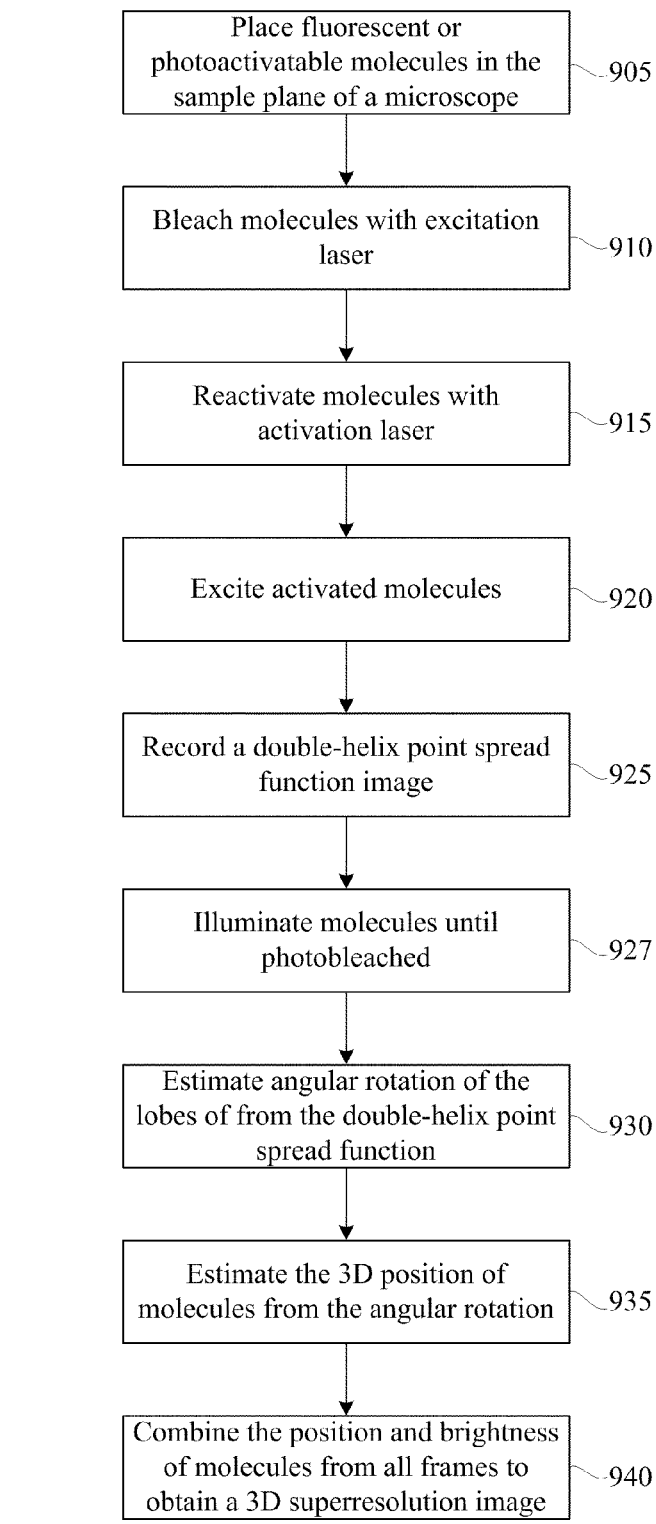
FIG. 9 is a flowchart of a process for estimating molecular position in three dimensions using a double-helix point spread function according to some embodiments of the invention.

FIG. 9 is a flowchart of process 900 for estimating molecular dimensions using a double-helix point spread function according to some embodiments of the invention. At block 905 a fluorescent molecule or molecules can be placed within the sample plane of microscope. The microscope can include a double-helix point spread function. The microscope can include the microscope shown in FIG. 5A. In some embodiments the molecule(s) can include any type of fluorescent molecules, such as any photoactivatable, blinkable, and/or photoswitchable molecule(s).

At block 910 the molecule(s) can be bleached with excitation light, for example, using a laser with an appropriate spectrum or wavelength. In some embodiments, block 910 can occur prior to block 905. At block 915 the molecule(s) can be activated with an activation light, for example, using a laser with an appropriate spectrum or wavelength to achieve conversion of the molecule to fluorescent form. At block 920 the molecule(s) can be excited to detect the molecule(s) and at block 925 double-helix point spread function images can be recorded. At block 927 the molecules can be irradiated until they are photobleached.

The angular rotation of the lobes in the double-helix point spread function can then be estimated. For example, this rotation can be estimated using methods described in this disclosure. From the angular rotation, the 3D position of the imaged molecule can be determined. Blocks 915, 920, 925, 927, 930, and 935 can be repeated as necessary to ensure an image of every molecule is recorded and the 3D position determined. At block 940 the position and brightness of all the molecules can be combined from all the images to create a 3D superresolution image. Various image or mathematical corrections can be made to provide better results.

Computational Device

FIG. 10 shows a block diagram of a computational device that can be used to determine position from images of a molecule according to some embodiments. In some embodiments of the invention, computational device 1000 can be used to perform the process shown in FIG. 9. The drawing illustrates how individual system elements can be implemented in a separated or more integrated manner. The computational device 1000 is shown having hardware elements that are electrically coupled via bus 1026. The hardware elements can include processor 1002, imager control output 1004, imager input 1006, storage device 1008, computer-readable storage media reader 1010a, communications system 1012, illumination control output 1014, processing acceleration unit 1018, such as a DSP or special-purpose processor, and memory 1018. Communications system 1012 can communicatively couple the computational device 1000 with another computer, for example, using USB, Bluetooth, or WiFi. The computer-readable storage media reader 1010a can be further connected to a computer-readable storage medium 1010b, the combination comprehensively representing remote, local, fixed, and/or removable storage devices plus storage media for temporarily and/or more permanently containing computer-readable information. In some embodiments, storage device 1008, computer-readable storage medium 1010b, and memory 1019 can all be portions of the same memory and can be used to store image data, dimensional data and/or executable programs.

Computational device 1000 can also include software elements, shown as being currently located within working memory 1020, including an operating system 1024 and other code 1022, such as a program designed to implement methods and/or processes described herein. In some embodiments, other code 1022 can include software that can be used to store images produced, for example, from the imager in the optical system shown in FIG. 5A. Illumination control output 1014 can be used to control the timing and duration of an imaging device that provides light at the proper wavelength so that fluorescing molecules will activate. Imager control output 1004 can be used to control operation of an imager (e.g., imager 540 of FIG. 5A).

Double-Helix Point Spread Functions

Figure 11:
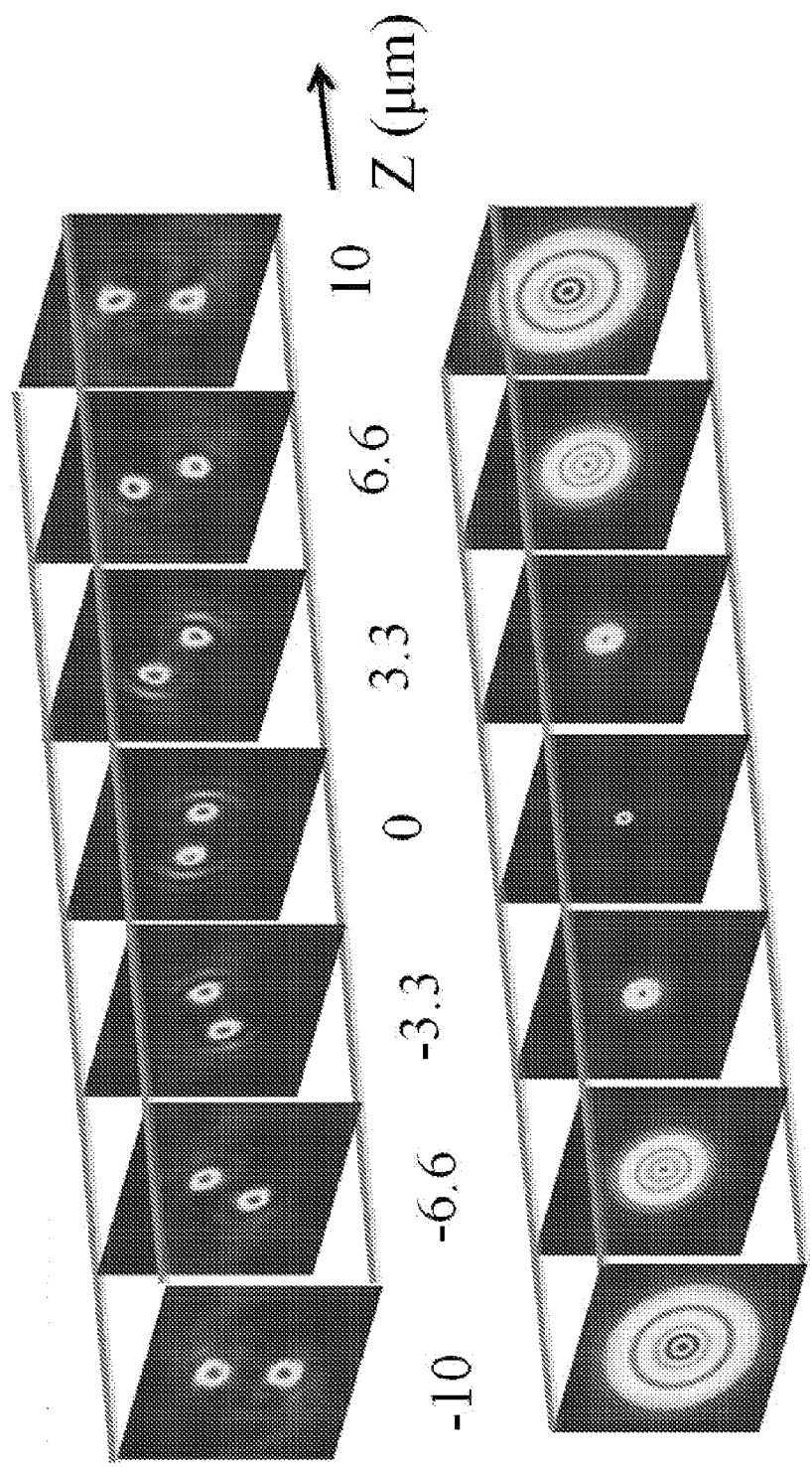
FIG. 11 shows a comparison of the responses of a standard point spread function and a double-helix point spread function.

Some embodiments of the invention utilize double-helix point spread functions. A double-helix point spread function system can be implemented by introducing a phase mask in the Fourier plane of an imaging system. The phase mask can be designed such that its transmittance function generates a rotating pattern in the focal region of a Fourier transform lens. Specifically, the double-helix point spread function can exhibit two lobes that spin around the optical axis as shown in FIG. 11. Note that double-helix point spread function (top) displays a significant change of orientation with defocus over an extended depth. In contrast, the standard point spread function (bottom) presents a slowly changing and expanding symmetrical pattern throughout the same region.

Analysis

Movies from the camera can be exported by software as tiff stacks or other graphical files. Two methods were used to determine the center position of each lobe of the double-helix point spread function. A threshold was applied to remove background, and then the center position of each lobe of the double-helix point spread function was determined using either a least-squares Gaussian fit or a simple centroid calculation. The midpoint of the two centroids gave the x and y position of the emitter and the angle of the line connecting the two centroids with respect to the horizontal gave the axial position after conversion from degrees to nanometers using the calibration curve in FIG. 5B.

The average number of photons detected in each case were obtained by summing the fluorescence counts in a background corrected image coming from a molecule and then converting the A/D counts into photons. The conversion gain of our camera, 24.7 $e^-$/count, was calibrated by a method described in the Supporting Information and the electron multiplication gain was calibrated to be 224.5 by measuring the increase in detected signal with gain versus that for no gain.

What is claimed is:

1. A method comprising:
illuminating with an illumination system of an imaging system a molecule within a sample near a focal plane of the imaging system;
directing light from the molecule toward an optical element comprising a double-helix point spread function;
imaging a point spread produced by the double-helix point spread function as a response to the molecule's emission;
determining, with a processor, an angular rotation of the point spread relative to a baseline rotation;
determining, with a processor, the distance between the molecule and the focal plane from the angular rotation; and
generating an output that when displayed specifies an estimated position of the molecule within the sample.

2. The method according to claim 1 wherein the double-helix point spread function is created using an iterative optimization procedure operating in more than one domain.

3. The method according to claim 2, wherein the domains comprise the GL modal plane, the Fourier plane, and the spatial plane.

4. The method according to claim 1 further comprising determining the lateral location relative to an optical axis from the centroid of the point spread.

5. The method according to claim 1, wherein the determining an angular rotation comprises:
- finding a center of each of two lobes of the point spread function using a least-squares fit;
- determining the midpoint between the two lobe centers; and
- determining the angle between the two centers.

6. The method according to claim 1, wherein the determining an angular rotation comprises determining the center of two lobes of the point spread function using one of either a centroid calculation or a Gaussian fit.

7. The method according to claim 1, wherein the distance between the molecule and the focal plane can be determined with an accuracy of about 5-50 nm.

8. The method according to claim 1, wherein the point spread function is a double-helix point spread function.

9. The method according to claim 1, wherein the determining the angular rotation of the point spread determines the rotation of one or more lobes of the point spread.

10. The method according to claim 1 wherein the double-helix point spread function comprises a phase mask.

11. The method according to claim 1 further comprising fluorescent molecules.

12. A fluorescence microscope comprising:
- an illumination system configured to illuminate a fluorescing molecule at an illumination wavelength;
- an optical system configured to image the fluorescing molecule at an imaging wavelength, wherein the imaging wavelength is different than the illumination wavelength;
- a double-helix point spread function disposed within the optical system, the double-helix point spread function configured to produce a double-helix point spread that rotates as a function of the fluorescing material's distance from a focal plane;
- an imager configured to produce an image of the double helix point spread; and
- a processor configured to:
  - determine an angular rotation of a double-helix point spread in the image,
  - determine a distance between the fluorescing material and an focal plane using the angular rotation; and
  - output the distance between the fluorescing material and the focal plane.

13. The fluorescence microscope according to claim 12, wherein the double-helix point spread function is created using an iterative optimization procedure operating in more than one domain.

14. The fluorescence microscope according to claim 13, wherein the three domains comprise the GL modal plane, the Fourier plane, and the spatial plane.

15. The fluorescence microscope according to claim 12 wherein the double-helix point spread function is disposed within either or both of a phase mask or a spatial light modulator.

16. The fluorescence microscope according to claim 12 further comprising a polarizer disposed between the double-helix point spread function and the imaging device.

17. A method comprising:
- receiving from an imager of an optical system a dual lobe image of a molecule through a double helix point spread function disposed within the optical system;
- determining a point of maximum intensity of each lobe;
- determining, with a processor, the angular rotation of the lobes using the center point;
- determining, with a processor, the position of the molecule from the angular rotation of the lobes; and
- outputting at least one of an x-coordinate, a y-coordinate, and a z-coordinate that specifies the position of the molecule.

18. The method according to claim 17, wherein the determining the center point of the lobes comprises finding the midpoint between the two center points.

19. The method according to claim 17, wherein the determining the center point of the lobes comprises using a centroid fit algorithm.

* * * * *